(12) United States Patent
Cashman et al.

(10) Patent No.: US 7,435,540 B2
(45) Date of Patent: Oct. 14, 2008

(54) PRP$^{SC}$-SELECTIVE PEPTIDES

(75) Inventors: Neil Cashman, Toronto (CA); Eustache Paramithiotis, Boucherville (CA); Sylvie La Boissière, Montreal (CA); Robert Lawton, Gorham, ME (US); Greg Francoeur, deceased, late of North Yarmouth ME (US); by Susan Francoeur, legal representative, Portland, ME (US); Lisa Estey, Westbrook, ME (US); Marc Pinard, Montreal (CA)

(73) Assignee: IDEXX Corporation, Westbrook, ME (US)

( * ) Notice: Subject to any disclaimer, the term of this patent is extended or adjusted under 35 U.S.C. 154(b) by 190 days.

(21) Appl. No.: 11/342,208

(22) Filed: Jan. 27, 2006

(65) Prior Publication Data

US 2006/0183156 A1 Aug. 17, 2006

Related U.S. Application Data

(62) Division of application No. 10/256,538, filed on Sep. 27, 2002, now abandoned.

(51) Int. Cl.
*G01N 33/53* (2006.01)
*G01N 33/566* (2006.01)
(52) U.S. Cl. .................. 435/5; 424/130.1; 424/139.1
(58) Field of Classification Search ............... None
See application file for complete search history.

(56) References Cited

U.S. PATENT DOCUMENTS

| 4,806,627 | A | 2/1989 | Wisniewski et al. |
|---|---|---|---|
| 5,597,725 | A | 1/1997 | Suzuki |
| 5,639,634 | A | 6/1997 | Suzuki |
| 5,643,781 | A | 7/1997 | Suzuki |
| 5,646,250 | A | 7/1997 | Suzuki |
| 5,663,300 | A | 9/1997 | Suzuki |
| 5,679,530 | A | 10/1997 | Brentani et al. |
| 5,708,143 | A | 1/1998 | Suzuki |
| 5,750,361 | A | 5/1998 | Prusiner et al. |
| 5,773,572 | A | 6/1998 | Fishleigh et al. |
| 5,798,224 | A | 8/1998 | Suzuki |
| 5,846,533 | A | 12/1998 | Prusiner et al. |
| 5,891,641 | A | 4/1999 | Prusiner et al. |
| 5,891,706 | A | 4/1999 | Suzuki |
| 6,355,610 | B2 | 3/2002 | Chesebro et al. |
| 6,451,541 | B1 | 9/2002 | Winnacker et al. |
| 6,462,171 | B1 | 10/2002 | Soto-Jara et al. |
| 2004/0072236 | A1 | 4/2004 | Cashman et al. |

FOREIGN PATENT DOCUMENTS

| DE | 197 41 607 A1 | 3/1999 |
|---|---|---|
| EP | 0 861 900 A1 | 9/1998 |
| SU | 1529119 A1 | 12/1989 |
| WO | WO 87/06706 | 11/1987 |
| WO | WO 92/06220 | 4/1992 |
| WO | WO 92/08731 | 5/1992 |
| WO | WO 93/11155 | 6/1993 |
| WO | WO 93/23432 | 11/1993 |
| WO | WO 94/01116 | 1/1994 |
| WO | WO 96/32128 | 10/1996 |
| WO | WO 96/39834 | 12/1996 |
| WO | WO 97/10505 | 3/1997 |
| WO | WO 97/16728 | 5/1997 |
| WO | WO 97/43649 | 11/1997 |
| WO | WO 97/45746 | 12/1997 |
| WO | WO 98/37210 | 8/1998 |
| WO | WO 99/15651 | 4/1999 |
| WO | WO 99/19360 | 4/1999 |
| WO | WO 99/42829 | 8/1999 |
| WO | WO 00/78344 | 12/2000 |
| WO | WO 00/78344 A1 | 12/2000 |
| WO | WO 01/00235 | 1/2001 |

OTHER PUBLICATIONS

Korth et al., "Acridinie and phenothiazine derivatives as pharmacotherapeutics for prion disease", Proc. Natl. Acad. Sci USA 98:9836-9841 (2001).
Ma et al., "Molecular dynamics simulations of alanine rich beta-sheet oligomers: Inshight into amyloid formation" Prot. Sci. 11:2335-2350 (2002).
Zou, et al., "All or none fibrillogenesis of a prion peptide", Eur. J. Biochem. 268:4885-4891 (2001).
International search report No. PCT/US03/30273 mailed Oct. 19, 2005.
West et al., "De novo amyloid proteins from designated combinatorial libraries", Proceedings of the National Academy of Science (1999) vol. 96, pp. 11211-11216.
Medline Accession #AAA67439 dated May 25, 1995.
Bradley, "BSE Transmission Studies with Particular Reference to Blood", Dev. Biol. Stand. 99:35-40 (1999).
Cai, et al., "Solvent-Dependent Precipitation of Prion Protein", Biochimica et Biophysica Acta 1597:28-35 (2002).
Cashman et al., "A Prion-Specific Immunological Epitope," Abstracts of the Society for Neuroscience 27:1743 (2001).
Caughey, "Probing for Prions: Recognizing Misfolded PrP", Nature Medicine 9:819-820 (2003).
Come et al., "A Kinetic Model for Amyloid Formation in the Prion Diseases: Importance of Seeding", Proc. Natl. Acad. Sci. USA 90:5959-5963 (1993).

(Continued)

*Primary Examiner*—Bruce Campell
*Assistant Examiner*—Michelle Horning
(74) *Attorney, Agent, or Firm*—McDonnell Boehnen Hulbert & Berghoff LLP

(57) ABSTRACT

The present invention features methods for identifying peptides that selectively bind to PrP$^{Sc}$ or fragments thereof. The invention also features the use of such peptides in screening methods for the identification of candidate agents useful for the treatment of a prion disease.

16 Claims, 4 Drawing Sheets

OTHER PUBLICATIONS

Demart et al., "New Insight into Abnormal Prion Protein Using Monoclonal Antibodies", Biochem. Biophys. Res. Commun. 165:652-657 (1999).

Gorochov et al., "Properties of a Disease Specific Prion Probe", Nature Medicine 10:11 (2004).

Krasemann et al., "Generation of Monoclonal Antibodies Against Human Prion Proteins in PrP0/0 mice", Mol. Med. 2:725-734 (1996).

Krasemann et al., "Induction of Antibodies Against Human Prion Proteins (PrP) by DNA-mediated Immunization of PrP0/0 Mice", J. Immunol. Methods 199:109-118 (1996).

Krasemann et al., "Generation of Monoclonal Antibodies Against Prion Proteins with an Unconventional Nucleic Acid-based Immunization Strategy", J. Biotechnol. 73:119-129 (1999).

Meggio, et al., "Bovine Prion Protein as a Modulator of Protein Kinase CK2", Biochem. J. 352:191-196 (2000).

Morel et al., "Selective and Efficient Immunoprecipitation of the Disease-Associated Form of the Prion Protein can be Mediated by Nonspecific Interactions Between Monoclonal Antibodies and Scrapie-Associated Fibrils", J. Biol. Chem. 279:30143-30149 (2004).

Paramithiotis et al., "Properties of a Disease Specific Prion Probe, Reply", Nature Medicine 10:11-12 (2004).

Paramithiotis et al., "A Prion Protein Epitope Selective for the Pathologically Misfolded Conformation", Nature Medicine 9:893-899 (2003).

Serbec et al., "Monoclonal Antibody against a Peptide of Human Prion Protein Discriminates between Creutzfeldt-Jacob's Disease-Affected and Normal Brain Tissue", J. Biol. Chem. 279:3694-3698 (2004).

Vorberg, et al., "A Novel Eptiope for the specific Detection of Exogenous Prion Proteins in Transgenic Mice and Transfected Murine Cell Lines", Virology, 255:26-31 (1999).

Zou et al., "Acidic pH and Detergents Enhanced In Vitro Conversion of Human Brain PrPcto to a PrPsc- like form", J. Biol. Chem. 277:43942-43947 (2002).

Zou et al., "Antibody to DNA Detects Scrapie but not Normal Prion Protein", Proc. Natl., Acad. Sci USA 3:1380-1385 (2004).

Arrou et al., "Enantioselective Separation of Basic Amino Acids on Talc", J. Chem. Tech. Biotechnol. 63:92-96 (1995).

Chadha, et al., "Heparin Binding Sites on Prions", Int. J. of Bio-Chromotography 2:211-223 (1997).

Lindon et al., "Separation and Characterization of Components of Peptide Libraries", Magn. Reson. Chem. 33:857-863 (1995).

Steiner, T., "Structural Evidence for the Aromatic -(/+1) Amine Hydrogen Bond in Peptides: L-Tyr-L-Tyr-L-Leu Monohydrate", Acta. Cryst. D54, 584-588 (1998).

Bacon and Anderson, "Multiple Sequence Alignment", J. Mol. Biol., 191:153-161 (1986).

Bendheim et al., "Antibodies to a Scrapie Prion Protein", Nature 310:418-421 (1984).

Bennet et al., "3D Domain swapping: A mechanism for oligomer assembly", Protein Science 4:2455-2468 (1995).

Bolton et al., "Identification of a Protein that Purifies with the Scrapie Prion", Science 218:1309-1311 (1982).

Bolton and Bendheim, "A modified host protein model of scrapie", Ciba Found. Symp. 135:164-177 (1988).

Brown et al., "Iatrogenic Creutzfeldt-Jakob disease at the millennium", Neurology 55:1075-1081 (2000).

Bueler et al., "Mice Devoid of PrP Are Resistant to Scrapie", Cell 73:1339-1347 (1993).

Bueler et al., "Normal development and behaviour of mice lacking the neuronal cell-surface PrP protein", Nature 356:577-582 (1992).

Cashman, "A prion primer", Canadian Medical Association Journal 157:1381-1385 (1997).

Cashman et al., "Cellular Isoform of the Scrapie Agent Protein Participates in Lymphocyte Activation", Cell 61:185-192 (1990).

Caughey et al., "Binding of the Protease-Sensitive Form of Prion Protein PrP to Sulfated Glycosaminoglycan and Congo Red", Journal of Virology 68:2135-2141 (1994).

Chandler, "Encephalopathy in Mice Produced by Inoculation with Scrapie Brain Material", Lancet 6:1378-1379 (1961).

Chemical Abstract 122:49358 CA (XP-002056077) (1992).

Cheng etal., "Identification and Cloning of ELF-1, a Developmentally Expressed Ligand for the Mek4 and Sek Receptor Tyrosine Kinases", Cell 79:157-168 (1994).

Collinge, "Variant Creutzfeldt-Jakob disease", Lancet 354:317-323 (1999).

Collinge, et al., "Prion protein is necessary for normal synaptic function", Nature 370:295-297 (1994).

Coulthart and Cashman, "Variant Creutzfeldt-Jakob disease: a summary of current scientific knowledge in relation to public health", Canadian Medical Association Journal 165:51-58 (2001).

Dayhoff, et al., "A Model of Evolutionary Change in Proteins", Atlas Protein Sequence and Structure 5:345-352 (1978).

Dodelet, et al., "Construction and Use of a Prion Protein-Alkaline Phosphatase Fusion Protein for Prion Ligand Detection", Cold Spring Harbor Laboratory, 61st Symposium: Function and Dysfunction in the Nervous System, May 29, 1996.

Eklund et al., "Pathogenesis of Scrapie Virus Infection in the Mouse", J. Infectious Disease 117:15-22 (1967).

Endo et al., "Diversity of Oligosaccharide Structures Linked to Asparagines of the Scrapie Prion Protein", Biochemistry 28:8380-8388 (1989).

Engleman, et al., "Identifying Nonpolar Transbilayer Helices in Amino Acid Sequences of Membrane Proteins", Annu. Rev. Biophys. Chem. 15:321-353 (1986).

Field, "Slow Virus Infections of the Nervous System", Brit. J. Exp. Path. 8:129-239 (1969).

Fields et al., "The two-hybrid system: an assay for protein-protein interactions", TIG 10:286-292 (1994).

Fisher, "Vaccine in Mice Fights Brain Changes Tied to Alzheimer's", The New York Times, National p. A16, Jul. 8, 1999.

Flanagan, et al., "The kit Ligand: A Cell Surface Moecule Altered in Steel Mutant Fibroblasts", Cell 63:185-194 (1990).

Gomi et al., "Mice Devoid of the Glial Fibrillary Acidic Protein Develop Normally and Are Susceptible to Scrapie Prions", Neuron 14:29-41 (1995).

Harmeyer et al., "Synthetic Peptide Vaccines Yield Monoclonal Antibodies to Cellular and Pathological Prion Proteins of Ruminants", J. Gen. Virology 79:937-945 (1998).

Houston, et al., "Influence of preformed a-helix and a-helix induction on the activity of cationic antimicrobial peptides", J. Peptide Res. 52:81-88 (1998).

Houston et al., "Transmission of BSE by blood transfusion in sheep", Lancet 356:999-1000 (2000).

Horiuchi et al., "Inhibition of Interactions and Interconversions of Prion Protein Isoforms by Peptide Fragments from the C-terminal Folded Domain", J. Biol. Chem. 276:15489-15497 (2001).

Kondejewski et al., "Dissociation of Antimicrobial and Hemolytic Activies in Cyclic Peptide Diastereomers by Systemic Alterations in Amphipathicity", J. Biol. Chem. 274:13181-13192 (1999).

Korth et al., "Prion (PrPsc)-Specific Epitope Defined by a Monoclonal Antibody", Nature 390:74-77 (1997).

Kretzschmar et al., "Molecular Cloning of a Human Prion Protein cDNA", DNA 5:315-324 (1986).

Kurschner et al., "Analysis of interaction sites in homo- and heteromeric complexes containing Bcl-2 family members and the cellular prion protein", Molecular Brain Research 37:249-258 (1996).

Kurschner et al., "The Cellular Prion Protein (PrP) Selectively Binds to Bcl-2 in the Yeast Two-hybrid System", Molecular Brain Research 30:165-168 (1995).

Kyte et al., "A Simple Method for Displaying the Hydropathic Character of a Protein," J. Mol. Biol. 157:105-132 (1982).

Li et al., "The Expression and Potential Function of Cellular Prion Protein in Human Lymphocytes", Cell. Immunol. 207:49-58 (2001).

Mabbott et al., "T-lymphocyte activation and the cellular form of the prion protein", Immunology 92:161-165 (1997).

McGaughey et al., "π-Stacking Interactions", J. Biol. Chem. 273:15458-15463 (1998).

McKinley, et al., "A Protease-Resistant Protein in a Structural Component of the Scrapie Prion", Cell 35:57-62 (1983).

Merrifield, "Solid Phase Peptide Synthesis. I. The synthesis of a Tetrapeptide", J. Am. Chem. Soc. 85:2149-2154 (1963).

Moore et al., "Ataxia in Prion Protein (PrP)-deficient Mice is Associated with Upregulation of a Novel PrP-like Protein Doppel", J. Mol. Biol. 292:797-817 (1999).

Oesch et al., "A Cellular Gene Encodes Scrapie PrP 27-30 Protein", Cell 40:735-746 (1985).

Oesch, "Characterization of PrP binding proteins", Phil. Trans. R. Soc. Lond., Ser. B 343:443-445 (1994).

Oesch et al., "Identification of Cellular Proteins Binding to the Scrapie Prion Protein", Biochemistry 29:5848-5855 (1990).

Pattison, "The Emergence of Bovine Spongiform Encephalopathy and Related Diseases", Emerging Infectious Diseases 4:390-394 (1998).

Priola et al., "Prion Protein and the Scrapie Agent: In Vitro Studies in Infected Neuroblastoma Cells", Infectious Agents and Disease 3:54-58 (1994).

Prusiner et al., "Ablation of the prior protein (PrP) gene in mice prevents scrapie and facilitates production of anti-PrP antibodies", Proc. Natl. Acad. Sci. USA 90:10608-10612 (1993).

Prusiner et al., "Further Pruficiation and Characterization of Scrapie Prions", Biochemistry 21:6942-6950 (1982).

Prusiner, "Molecular Biology of Prion Diseases", Science 252:1515-1522 (1991).

Prusiner, "Novel Proteinaceous Infectious Particles Cause Scrapie", Science 216:136-144 (1982).

Prusiner, "Prions", Proc. Natl. Acad. Sci., USA 95:13363-13383 (1998).

Ricketts et al., "Is Creutzfeldt-Jakob Disease Transmitted in Blood", Emerging Infectious Diseases 3:155-163 (1997).

Sano et al., "Protocadherins: A Large Family of Cadherin-related Molecules in Central Nervous System", EMBO J. 12:2249-2256 (1993).

Schenk et al., "Immunization with Amyloid-β Attenuates Alzheimer-Disease-Like Pathology in the PDAPP Mouse", Nature 400:173-177 (1999).

Shapiro et al., "Structural Basis of Cell-cell Adhesion by Cadherins", Nature 374:327-337 (1995).

Shyng et al., "Sulfated Glycans Stimulate Endocytosis of the Cellular Isoform of the Prion Protein, PrPc, in Cultured Cells", Journal of Biological Chemistry 270:30221-30229 (1995).

St. George-Hyslop et al., "Antibody Clears Senile Plaques" Nature 400:116-117 (1999).

Swietnicki et al., "pH-dependent Stability and Conformation of the Recombinant Human Prion Protein PrP(90-231)", J. Biol. Chem., 272:27517-27520 (1997).

Tam et al., "Membranolytic selectivity of cystine-stabilized cyclic protegrins", Eur. J. Biochem. 267:3289-3300 (2000).

Tam and Zavala, "Multiple antigen peptide", J. Immunol. Methods 124:53-61 (1989).

Tam, "Recent advances in multiple antigen peptides", J. Immunol. Methods 196:17-32 (1996).

Tam "Synthetic peptide vaccine design: Synthesis and properties of a high-density multiple antigenic peptide system", Proc. Natl. Acad. Sci., USA 85:5409-5413 (1988).

Tatzelt et al., "Scrapie in Mice Deficient in Apolipoprotein E or Glial Fibrillary Acidic Protein", Neurology 47:449-453 (1996).

Taylor et al., "Infectivity in the blood of mice with a BSE-derived agent", J. Hosp. Infect. 46:78-79 (2000).

Telling et al., "Prion Propagation in Mice Expressing Human and Chimeric PrP Transgenes Implicates the Interaction of Cellular PrP with Another Protein", Cell 83-79-90 (1995).

Tobler et al., "Sleep and Sleep Regulation in Normal and Prion Protein-Deficient Mice", J. Neuroscience 17:1869-1879 (1997).

Weiss et al., "Overexpression of Active Syrian Golden Hamster Prion Protein $PrP_c$ as a Glutahione-S-Transferase fusion in Heterologous Systems", Journal of Virology 69:4776-4783 (1995).

Westaway et al., "Degeneration of Skeletal Muscle, Peripheral Nerves, and the Central Nervous System in Transgenic Mice Overexpressing Wild-Type Prion Proteins", Cell 76:1.17-129 (1994).

Will et al., "A new variant of Creutzfeldt-Jakob disease in the UK", Lancet 347:921-925.

Yehiely et al., "Identification of Candidate Proteins Binding to Prion Protein", Neurobiology of Disease 3:339-355 (1997).

GenBank Accession No. P04156 dated Nov. 1, 1986.
GenBank Accession No. P04925 dated Aug. 13, 1987.
GenBank Accession No. P23907 dated Nov. 1, 1991.
GenBank Accession No. P52113 dated Oct. 1, 1991.
GenBank Accession No. O02841 dated Sep. 13, 2005.
GenBank Accession No. P79142 dated Mar. 15, 2004.
GenBank Accession No. P10279 dated Mar. 1, 1989.
GenBank Accession No. Q01880 dated Jun. 1, 1994.
GenBank Accession No. O18754 dated Jul. 15, 1998.
GenBank Accession No. P97895 dated Oct. 1, 2003.
Medline Accession #P80419 dated Apr. 18, 2006.
Medline Accession #P80421 dated Apr. 18, 2006.
Medline Accession #1CU4L dated Aug. 20, 1999.
Medline Accession #1CU4H dated Aug. 20, 1999.
Medline Accession #AAY78442 dated Jun. 13, 2005.

PRP$^{SC}$-SELECTIVE PEPTIDES

PRIORITY

This application is a divisional application of U.S. application Ser. No. 10/256,538, filed Sep. 27, 2002 now abandoned, which is incorporated herein by reference in its entirety.

BACKGROUND OF THE INVENTION

This invention relates to molecules (for example, peptides) that bind selectively to the disease-specific abnormal isoform of the prion protein, herein generically designated PrP$^{Sc}$, and not to the normal isoform of this protein, designated PrP$^C$. These molecules are useful for detecting PrP$^{Sc}$ in a sample, and for purifying PrP$^{Sc}$. Additionally, the invention relates to diagnostic aids for the detection of PrP$^{Sc}$, pharmaceuticals that inhibit the recruitment of normal PrP$^C$ to the disease-specific PrP$^{Sc}$, and methods for prion decontamination.

The prion diseases are a group of rapidly progressive, fatal, and untreatable neurodegenerative syndromes. Human prion diseases include classical Creutzfeldt-Jakob disease (CJD), which has sporadic, iatrogenic, and familial forms. More recently, a variant CJD (vCJD) has been recognized in the United Kingdom, France, the Republic of Ireland, Hong Kong, Italy and the United States (Will et al., Lancet 347:921-25, 1996; Collinge, Lancet 354:317-23, 1999), likely derived from the consumption of cattle tissues contaminated with the agent of bovine spongiform encephalopathy ("BSE"; reviewed in Cashman, Can. Med. Assoc. J. 157:1381-5, 1997; Coulthart and Cashman, Can. Med. Assoc. J. 165:51-8, 2001). More than 173,000 cattle, primarily from Britain, have developed symptomatic BSE, and many thousands more have probably entered the food supply undetected. The primary epidemic of vCJD has been predicted to range from dozens to hundreds of thousands of afflicted individuals, based on various poorly understood assumptions, such as the incubation period of the disease. Moreover, classical CJD has been accidentally transmitted between humans by contaminated cadaveric pituitary hormones, dura mater transplantation, neurosurgical instrumentation, and corneal transplantation (Brown et al., Neurology 55:1075-8, 2000). A "secondary epidemic" of vCJD through blood and blood products, general surgery, dentistry, vaccines, and cosmetics cannot be ruled out at present. The detection of blood prion infectivity in experimental BSE/vCJD infections of mice and sheep (Taylor et al., J. Hosp. Infect. 46:78-9, 2000; Houston et al., Lancet 356:999-1000, 2000), but not in classical CJD (Rickets et al., Emerg. Infect. Dis. 3:155-63,1997) suggests a special risk of transmitting vCJD through blood and blood products. The United States and Canada have now implemented a blood donor deferral for individuals who resided in the UK during the BSE epidemic, and Canada has also deferred donors from France. Donor deferrals extended to Western Europe are now being implemented in the United States and Canada.

Prions are the infectious agents that are associated with the transmissible spongiform encephalopathies noted above. The prion diseases are neurodegenerative syndromes characterized by spongiform change (e.g., microcavitation of the brain, usually predominant in gray matter), neuronal cell loss, astrocytic proliferation disproportionate to neuronal loss, and accumulation of an abnormal amyloidogenic protein, sometimes in discrete plaques in the brain. The agents that transmit these diseases differ markedly from viruses and viroids in that no chemical or physical evidence for a nucleic acid component has been reproducibly detected in infectious materials (Prusiner, Science 216: 136-144, 1982). A major step in the study of model scrapie prions was the discovery and purification of a protein designated the scrapie-associated prion protein (PrP$^{Sc}$) (Bolton et al., Science 218:1309-11, 1982; Prusiner et al., Biochemistry 21:6942-50, 1982; McKinley et al., Cell 35:57-62, 1983). When purified using proteinase K digestion, a 27-30 kD protease-resistant protein was discovered in scrapie-affected hamster brain, and was termed PrP 27-30, later found to be a fragment of PrP$^{Sc}$ (Bolton et al., Science 218:1309-1311, 1982).

According to the prion hypothesis, prion infectivity resides in PrP$^{Sc}$, or a related conformational intermediate. PrP$^{Sc}$ is the most prominent (or perhaps sole) macromolecule in preparations of prion infectivity, and appears to be at least a reliable surrogate for most prion infection. PrP$^{Sc}$ is a conformational variant of a host-encoded cellular protein designated PrP$^C$ (Oesch et al., Cell 40:735-746, 1985), which is a glycosylphosphatidylinositol (GPI)-linked cell surface protein with a molecular mass of 33-35 kD. PrP$^C$ has been isolated from normal brain, and has been found to be protease-sensitive and not associated with scrapie disease-producing activity (Bolton and Bendheim Ciba Found. Symp. 135:164-177, 1988). According to the prion theory, PrP$^C$ converts into PrP$^{Sc}$ in a template-directed process initiated by contact with PrP$^{Sc}$ (Prusiner, Proc. Natl. Acad. Sci., U.S.A. 95:13363-83, 1998).

PrP$^C$ is an evolutionarily conserved membrane protein for which the actual biological or physiological function is unclear. Mice devoid of PrP$^C$ are viable and show no obvious signs of neurological and physical impairment (Bueler et al., Nature 356:577-582, 1992), except for an ataxic syndrome in certain PrP knockout mouse strains due to upregulation in brain of the prion homolog protein dopple (Moore et al., J Mol. Biol. 292:797-817, 1999). Prnp knockout mice are not susceptible to prion infection, underscoring the central importance of PrP$^C$ in the replication of infectivity (Bueler et al., Cell 73:1339-1347, 1993; Prusiner et al., Proc. Natl. Acad. Sci., U.S.A. 90:10608-10612, 1993). Targeted investigations of Prnp knockout mice revealed impaired synaptic function (Collinge et al., Nature 370:295-297, 1994) and altered sleep regulation (Tobler et al., J. Neurosci. 17:1869-79, 1997). Moreover, antibody-mediated ligation of PrP$^C$ at the cell surface has been shown to depress T cell activation (Cashman et al., Cell 61:185-192, 1990; Li et al., Cell. Immunol. 207:49-58 2001), suggesting a role for the protein in immune function.

PrP$^C$ is present in large excess to PrP$^{Sc}$ in accessible peripheral tissues and organs of animals and humans afflicted with prion diseases. The availability of reagents that distinguish PrP$^{Sc}$ from PrP$^C$ would therefore be of great value in development of a test for prion infection in blood or other tissues accessible to sampling. Furthermore, in view of the epidemic nature of BSE and vCJD, a pressing need exists for therapeutic agents that prevent and/or treat prion diseases. Accordingly, a need exists in the art for testing samples for the presence of prions, methods for treating prion diseases, as well as for developing anti-prion pharmaceuticals and decontaminants.

SUMMARY OF THE INVENTION

As is described in greater detail below, we have developed a method to exploit the distinctive physiochemical properties of PrP$^{Sc}$ (and its protease-resistant fragment PrP 27-30) to identify molecules (e.g., peptides) which selectively bind to these conformationally abnormal isoforms, without binding to the normal isoform which is usually present in great excess in biological fluids and tissues.

The invention therefore relates to methods for identifying molecules (e.g., peptides) that selectively bind to PrP$^{Sc}$, exploiting surface hydrophobicity, charge interactions, and beta-sheet converting potential of peptides in their affinity reactions with PrP$^{Sc}$. For example, a subset of these molecules, such as peptides, are defined by amino acid sequences within the prion protein sequence itself and/or by evolutionarily conserved amino acid substitutions to these sequences. Other peptides are those that bind selectively to regions of PrP$^{Sc}$ (such as those regions of the protein that include YYX amino acid residues) based on physicochemical interactions such as hydrophobic interactions, pi-stacking, or beta sheet interactions. Peptides selectively binding PrP$^{Sc}$ may be constrained by cyclization, and by formation of hairpins or loops by introduction of cysteines to form disulfide bonds upon oxidation. For use in a diagnostic test of prion infection, peptides can be covalently coupled to a solid substrate, such as agarose beads, magnetic beads, or ELISA plates, reacted with a sample containing PrP$^{Sc}$, cleared of PrP$^{C}$ by washing (with or without proteinase K), so that detection of bound PrP$^{Sc}$ can be efficiently and specifically accomplished with a PrP$^{Sc}$-specific antibody, or with a non-distinguishing antibody or molecule binding both PrP$^{Sc}$ and PrP$^{C}$. Such peptides are also useful in concentrating PrP$^{Sc}$ from biological samples.

Peptides of the invention are suitable for therapeutic, diagnostic, or decontamination purposes. In a preferred embodiment, the molecular weight of the peptide is from about 40,000 Daltons to about 300 Daltons. Other peptides may fall in a narrower range, for example, 30,000 to about 1,000 Daltons, or from about 20,000 to about 2,000 Daltons. Peptides of the invention may be synthesized according to standard methods known in the art.

In a related embodiment, the invention is directed to a detectably-labeled peptide as described herein, the peptide preferably having a covalently attached label capable of detection.

In still other embodiments, the peptides are linked to a spacer having multiple side chain amines, such as poly(l-ysine), can be used to "amplify" the available surface functionalities. Multiple antigen peptide system ("MAPS") peptides typically consist of a branched lysine core matrix (Tam, Proc Natl Acad Sci U.S.A. 85: 5409-13, 1988; Tam and Zevala, J. Immunol Methods 124: 53-61, 1989; Tam, J. Immunol Methods 196: 17-32, 1996). The branched lysine core provides a scaffolding to support multiple copies of any of the peptides described herein.

Accordingly, in a first aspect, the invention features a method for identifying a peptide that binds to PrP$^{Sc}$ or a fragment thereof. This method includes the steps of (a) contacting a peptide of about 200 or fewer amino acids with a PrP$^{Sc}$ polypeptide or fragment thereof under conditions that allow for complex formation between the peptide and PrP$^{Sc}$ or fragment thereof, and (b) detecting the complex, wherein the presence of the complex identifies the peptide as one which selectively binds to PrP$^{Sc}$ or a fragment thereof. In preferred embodiments, the complex is detected using ELISA, RIA, western blotting, immunoprecipitation, fluorescence polarization or flow cytometry.

In preferred embodiments, the peptide is a fragment of PrP. In additional preferred embodiments, the peptide can range in chain length from 100 to 150 amino acids, more preferably 50 to 100 amino acids, or 25 to 50 amino acids, and most preferable 9 to 25 amino acids. The peptide can also be a tripeptide, a tetrapeptide, a pentapeptide, a hexapeptide, a heptapeptide, an octapeptide, a nonapeptide, or a decapeptide.

In preferred embodiments of the first aspect, the peptide can include a YYX (where X is any amino acid) or YSA motif, which can be repeated in the peptide (e.g., in tandem). The YYX motif can include the amino acids YYR, YYD, YYA, and YYQ. The peptide can also include a YYXXYYXYY (SEQ ID NO: 1) where X is any amino acid) motif. An example of a peptide with a YYXXYYXYY (SEQ ID NO: 1) motif is the peptide YYRRYYRYY (SEQ ID NO: 2).

In additional preferred embodiments, the peptide is coupled to a scaffolding agent, for example, a 4-map or an 8-map. The peptide can also be covalently coupled to a detectable-agent, solid support, or carrier.

The invention also features a method for detecting a PrP$^{Sc}$ in a biological sample. This method includes the steps of (a) contacting the biological sample with a peptide of about 200 or fewer amino acids which selectively binds to PrP$^{Sc}$ or a fragment thereof under conditions that allow for complex formation between the peptide and a PrP$^{Sc}$ polypeptide or fragment thereof, and (b) detecting the complex as an indication that PrP$^{Sc}$ is present in the biological sample.

In preferred embodiments, the peptide does not substantially bind PrP$^{C}$. The peptide can be 9 to 20 amino acids in length and can include a YYX, YYXXYYXYY (SEQ ID NO:1), or YSA motif. Preferred sequences for the YYX motif are YYR, YYD, YYA, and YYQ. In preferred embodiments, the peptide comprising the YYX sequence is covalently coupled to a detectable-label. The peptide comprising the YYX or YSA motif can also be covalently coupled to a solid support or carrier.

The biological sample includes any tissue or cell, tissue or cell extract, bodily fluid or biopsy. In preferred embodiments, the PrP$^{Sc}$ is from a human, a livestock species, or a pet species. In additional preferred embodiments, the PrP$^{Sc}$ from the biological sample is amplified PrP$^{Sc}$. Preferred methods of detection include ELISA, RIA, western blotting, immunoprecipitation, fluorescence polarization, and flow cytometry.

The present invention also includes methods for diagnosing a prion disease such as variant Creutzfeldt-Jakob Disease, bovine spongiform encephalopathy, scrapie, transmissible spongiform encephalopathy, and chronic wasting disease. This method includes the steps of (a) contacting a biological sample from a mammal with a peptide of about 200 or fewer amino acids which selectively binds to PrP$^{Sc}$ or a fragment thereof under conditions that allow for complex formation between the peptide and a PrP$^{Sc}$ polypeptide or fragment thereof and (b) detecting the complex which, if present, indicates a prion disease in the mammal.

In preferred embodiments, the peptide does not substantially bind PrP$^{C}$. In additional preferred embodiments, the peptide comprises a YYX, YSA, or YAR motif, wherein the YYX motif is selected from the group consisting of YYR, YYD, YYA, and YYQ. The peptide comprising a YYX motif can optionally be covalently coupled to a detectable-agent or a solid substrate.

For the diagnostic methods, it is preferred that the biological sample comprise a tissue or cell, a tissue or cell extract, a bodily fluid, or a biopsy and the PrP$^{Sc}$ is from a human, a livestock species, or a pet species. Detection of the complex is preferably achieved through the use of ELISA, RIA, western blotting, immunoprecipitation, fluorescence polarization, or flow cytometry.

The present invention also features methods for treating or preventing a prion disease in a mammal. This method includes the steps of administering to the mammal an effective amount of a peptide of about 200 or fewer amino acids which selectively binds to PrP$^{Sc}$ or a fragment thereof in a pharmaceutically-acceptable carrier and under conditions that allow for complex formation between the peptide and a PrP$^{Sc}$ poplypeptide or fragment thereof. A prion disease can be selected from the group consisting of variant Creutzfeldt-Jakob Disease, bovine spongiform encephalopathy, and scrapie.

In preferred embodiments, the peptide does not substantially bind to PrP$^C$. The peptide preferably comprises a YYX or YSA motif, wherein the YYX motif is selected from the group consisting of YYR, YYD, YYA, and YYQ.

Additional features of the invention include methods of inhibiting PrP$^{Sc}$ in a biological sample. This method comprises treating the biological sample with a peptide of about 200 or fewer amino acids which selectively binds to PrP$^{Sc}$ or a fragment thereof under conditions that allow for complex formation between the peptide and a PrP$^{Sc}$ polypeptide or fragment thereof and for a period of time sufficient to permit the formation of a complex comprising the peptide and a PrP$^{Sc}$.

In preferred embodiments, the biological sample is a bodily fluid, a tissue, or an organ. The biological sample is also preferably perfused with the peptide, which, in preferred embodiments, does not substantially bind to PrP$^{Sc}$.

The present invention also features a method for decontaminating PrP$^{Sc}$ from a biological sample. This method includes the steps of (a) treating the biological sample with a peptide of about 200 or fewer amino acids which selectively binds to PrP$^{Sc}$ or a fragment thereof under conditions that allow for complex formation between the peptide and a PrP$^{Sc}$ polypeptide or fragment thereof and for a period of time sufficient to permit the formation of a complex comprising the peptide and PrP$^{Sc}$, and (b) recovering the complex from the biological sample. The biological sample is preferably a tissue, bodily fluid or an organ and is perfused with the peptide.

In preferred embodiments, the peptide does not substantially bind PrP$^C$. In additional preferred embodiments, the peptide comprises a YYX or YSA motif, wherein the YYX motif is selected from the group consisting of YYR, YYD, YYA, and YYQ.

The present invention also features a method for identifying an agent for the treatment of a prion disease selected from the group consisting of variant Cruetzfeldt-Jakob Disease, bovine spongiform encephalopathy, and scrapie. The method includes the steps of (a) combining a peptide of about 200 or fewer amino acids which selectively binds to PrP$^{Sc}$ or a fragment thereof, PrP$^{Sc}$, and an agent under conditions allowing for complex formation of the peptide and the PrP$^{Sc}$, and (b) determining whether complex formation is increased or decreased in comparison to complex formation in the absence of the agent, thereby identifying an agent for treating the prion disease. The agent used can decrease or increase complex formation.

In preferred embodiments, the prion disease affects a human, a livestock species, or a pet species. Non-limiting examples of animals that can be affected by the prion disease include a human, a bovine, a sheep, or a goat.

In preferred embodiments, the peptide does not substantially bind PrP$^C$. In additional preferred embodiments, the peptide comprises a YYX or YSA motif, wherein the YYX motif is selected from the group consisting of YYR, YYD, YYA, and YYQ.

The present invention also features an apparatus for detecting PrP$^{Sc}$ in a biological sample. The apparatus comprises a peptide-fixed portion where a peptide for trapping an amount of an analyte in a sample is present and in a predetermined amount. In preferred embodiments of this aspect, the analyte is a bodily fluid.

In preferred embodiments, the peptide comprises a YYX, YYR, YYD, or YYQ amino acid sequence and has antigenicity as a PrP$^{Sc}$. The peptide can also have the amino acid sequence YYRRYYRYY (SEQ ID NO: 2) or YYR. The peptide is composed of 18 or fewer amino acids, preferably 12 or fewer amino acids, more preferably 8 or fewer amino acids, and most preferably 5 or fewer amino acids.

The invention also features a method for detecting an anti-PrP$^{Sc}$ antibody in a biological sample. This method comprises the steps of (a) contacting the biological sample with a peptide of about 200 or fewer amino acids which selectively binds to PrP$^{Sc}$ or a fragment thereof under conditions that allow for complex formation between the peptide and anti-PrP$^{Sc}$ antibody, and (b) detecting the complexes as an indication that anti-PrP$^{Sc}$ antibody is present in the biological sample.

By "peptide" is meant a molecule comprised of a chain of amino acid residues joined by peptide (i.e., amide) bonds and includes proteins and polypeptides. Peptides can be expected to possess conformational preferences and to exhibit a three-dimensional structure. Both the conformational preferences and the three-dimensional structure are typically defined by the polypeptide's primary (i.e., amino acid) sequence and/or the presence (or absence) of disulfide bonds or other covalent or non-covalent intrachain or interchain interactions. Exemplary peptides of the invention are those having a chain of 200 or fewer amino acids. Other peptides range from between 3 to 100 amino acids, or 9 to 25 amino acids. Exemplary peptides are obtained from PrP and typically include consensus sequences such as "YYX," "YYR, "YYQ," "YYD," or "YSA." The peptide can, if desired, be linked (e.g., covalently) to a detectable label for use as an affinity probe to immobilized PrP$^{Sc}$ (or a PrP$^{Sc}$ fragment). Other peptides can be random amino acid sequences that specifically bind to PrP$^{Sc}$ based on physicochemical interaction, for example, to regions of PrP$^{Sc}$ that include amino acid residues YYX. As is disclosed in greater detail below, the invention provides peptides that specifically bind to a PrP$^{Sc}$ protein and preferably bind to a native non-denatured PrP$^{Sc}$ protein at high affinity. Standard procedures for carrying out such affinity measurements are known in the art and can be directly applied to measure the affinity of a peptide of the invention for its binding to PrP$^{Sc}$. Preferred peptides of the invention are those that specifically bind to PrP$^{Sc}$, but do not substantially bind to PrP.

The selective binding affinity between a peptide and PrP$^{Sc}$ (or a fragment thereof) generally falls in the range of about 1 nM to about 1 mM. In preferred embodiments of the present invention, the selective binding is on the order of about 10 nM to about 100 μM, more preferably on the order of about 100 nM to about 10 μM, and most preferably on the order of about 100 nM to about 1 μM.

Systematic substitution of one or more amino acids of a consensus sequence with a D-amino acid of the same type (e.g., D-lysine in place of L-lysine) may also be used to generate more stable peptides. In addition, so-called constrained peptides comprising a consensus sequence, for example those described herein, or a substantially identical consensus sequence variation may be generated by methods known in the art. For example, by adding internal cysteine residues capable of forming intramolecular disulfide bridges which cyclize the peptide as is described by Tam et al. (Eur. J. Biochem. 267:3289-3300, 2000). The common modes of cyclization also include side chain to side chain cyclization or side chain to end-group cyclization as is described by Houston et al. (J. Peptide Res. 52:81-88, 1998). For this purpose, amino acid side chains are connected together or to the peptide backbone. Another common cyclization as is the end-to-end cyclization as is described in Kondejewski et al. (J. Biol. Chem. 274:13181-13192, 1999).

By "detectable label" is meant a material, which when covalently attached to the peptides of this invention, permits detection of the peptide. Suitable detectable labels are well known in the art and include, by way of example, radioisotopes, fluorescent labels (e.g., fluorescein), enzymes, epitope tags (e.g. FLAG and Myc) and the like. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$. The particular detectable label employed is not critical. Selection of the label relative to such factors is well within the skill of the art. Covalent attachment of the detectable label to the peptide is accomplished by conventional methods well known in the art. For example, when the $^{125}I$ radioisotope is employed as the detectable label, covalent attachment of $^{125}I$ to the peptide can be achieved by incorporating the amino acid tyrosine into the peptide and then iodating the peptide. If tyrosine is not present in the peptide, incorporation of tyrosine to the N or C terminus of the peptide can be achieved by well-known chemistry. Similarly, $^{32}P$ can be incorporated onto the peptide as a phosphate moiety through, for example, a hydroxyl group on the peptide using conventional chemistry. Other methods for detectably-labeling a peptide of the invention are well known in the art.

By "prion diseases" is meant a group of prion-mediated, rapidly progressive, fatal, and untreatable brain degenerative disorders including, without limitation, Creutzfeldt-Jakob disease (CJD), variant CJD, iatrogenic CJD, familial. CJD, Kuru, Gerstmann-Straussler syndrome, and fatal familial insomnia in humans (Prusiner, Science 252:1515-1522, 1991), scrapie in sheep and goats, and spongiform encephalopathy in cattle, as well as recently described prion diseases in other ruminants and cats (see, for example, Pattison, Emerg. Infect. Dis. 4:390-394, 1998).

By "treatment of prion diseases" is meant the ability to reduce, prevent, stabilize, or retard the onset of any symptom associated with prion diseases, particularly those resulting in spongiform change, neuronal cell loss, astrocytic proliferation, accumulation of PrP$^{Sc}$ protein, dementia, or death.

By "YYX" is meant a peptide having the sequence Tyrosine-Tyrosine-X, where X is any amino acid. By "YYR" is meant a peptide having the sequence Tyrosine-Tyrosine-Arginine. By "YYQ" is meant a peptide having the sequence "Tyrosine-Tyrosine-Glutamine." By "YYD" is meant a peptide having the sequence "Tyrosine-Tyrosine-Aspartic acid." By "YSA" is meant a peptide having the sequence Tyrosine-Serine-Alanine. By "YYA" is meant a peptide having the sequence Tyrosine-Tyrosine-Aspartic acid." By "YYR-RYYRYY" (SEQ ID NO:2) is meant a peptide having the sequence Tyrosine-Tyrosine-Arginine-Arginine-Tyrosine-Tyrosine-Arginine-Tyrosine-Tyrosine."

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Asparcic Acid is Asp or D; Glutamic Acid is Glu or E; Cysteine is Cys or C; Tryptophan is Trp or W; Arginine is Arg or R; and Glycine is Gly or G.

By a "therapeutic composition" is meant a composition appropriate for administration to an animal, for example, a mammal, such as a human, a livestock species (for example, a bovine, goat, pig, or sheep), or a pet species.

By a "small molecule" is meant a compound with a molecular weight of less than or equal to 10,000 Daltons, preferably, less than or equal to 1000 Daltons, and, most preferably, less than or equal to 500 Daltons.

Exemplary solid supports useful in the methods of the invention include magnetic beads or other beads (e.g., agarose), membranes (e.g. nitrocellulose, nylon), or plate wells (e.g., ELISA, or derivatized surfaces), carriers would generally be soluble substrates, such as proteins (such as albumin or thyroglobulin) or other soluble molecules.

The compounds (e.g., peptides) described herein are useful for the prevention and treatment of prion diseases, for example, those mediated by PrP$^{Sc}$.

The invention also provides for pharmaceutical compositions comprising one or more of the compounds described herein and a physiologically acceptable carrier. These pharmaceutical compositions can be in a variety of forms including oral dosage forms, as well as inhalable powders and solutions and injectable and infusible solutions.

Synthetic peptides can also be used directly to treat prion diseases, and medications useful in the prevention and treatment of prion diseases can be screened by inhibition of interactions between PrP$^{Sc}$ and PrP$^{Sc}$-binding peptides. PrP$^{Sc}$ can be adsorbed from biological fluids and tissues to neutralize prion infectivity prior to human use or as a prion disease prophylactic in animal feed. For example, the present invention further provides methods for identifying potential new drug candidates (and potential lead compounds) and methods for determining the specificities of these compounds. For example, knowing that a peptide exhibits a selective affinity to $PrP^{Sc}$ enables the identification of a compound that effects the binding between these molecules, e.g., either as an agonist or as an antagonist (inhibitor) of the interaction. With this assay, then, one can screen one or more libraries of candidate compounds to identify a compound exhibiting the most desired characteristic, e.g., the most efficacious in disrupting the interaction or in competing with the peptide for binding to $PrP^{Sc}$.

Such synthetic peptides also have utility as diagnostic reagents, and in therapy of prion diseases.

The invention further includes a solid support which includes a peptide that selectively binds $PrP^{Sc}$ in the form of a detection apparatus or device which comprises a chamber, one or more inlet ports, one or more outlet ports, and a matrix within the chamber to which the peptide is adsorbed or chemically crosslinked. In an illustrative embodiment, a peptide of the invention is adsorbed to a solid support, a solution containing $PrP^{Sc}$ is passed over the support, and non-binding components from the solution are removed, e.g., by washing. Methods for washing such a column, device, or apparatus to remove contaminating materials, and then subsequently eluting the bound $PrP^{Sc}$ from the peptide matrix using eluants such as chaotropic reagents are well known in the art. The apparatus of the invention provides detection systems for detecting, monitoring, quantitating or analyzing $PrP^{Sc}$ specifically retained on the surface of the platform, in a detection chamber comprising a specific binding reagent (e.g., a peptide that specifically binds $PrP^{Sc}$). Detection systems useful in the manufacture and use of the platforms of the invention include, but are not limited to, fluorescent, chemiluminescent, or radioactive measurements.

Other features and advantages of the invention will be apparent from the following description of the preferred embodiments thereof, and from the claims.

DETAILED DESCRIPTION OF INVENTION

Figure 1:
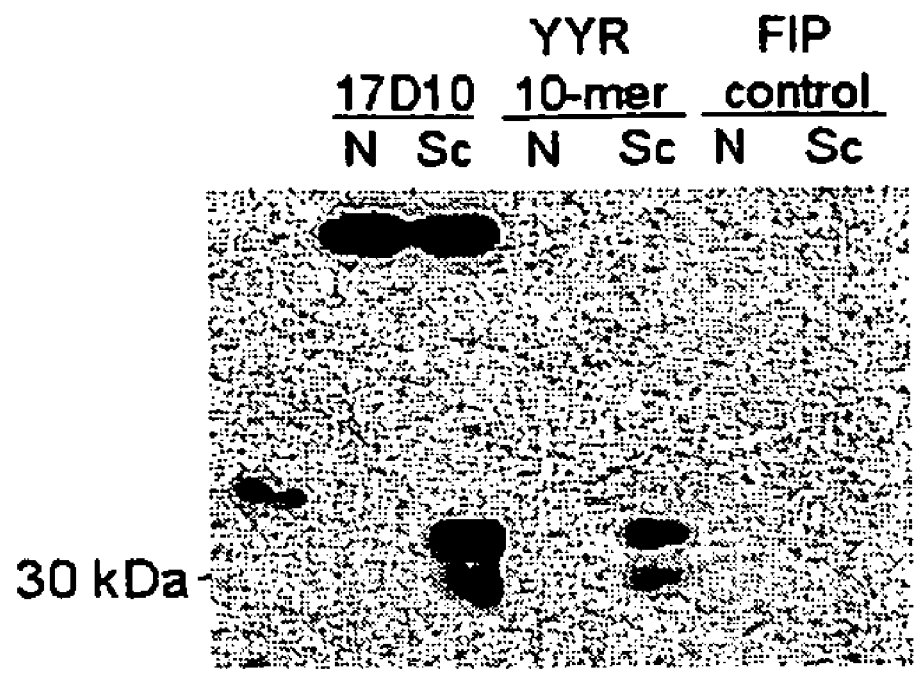
FIG. 1 shows that the YYRRYYRYY (SEQ ID NO:2) peptide captures PrP$^{Sc}$ in hamster brain lysates.

We describe below a method by which PrP$^{Sc}$-interacting molecules (e.g., peptides) can be recognized. Preferably, PrP$^{Sc}$-interacting molecules will be identified that exploit general physicochemical properties of PrP$^{Sc}$ which distinguish it from PrP$^C$, or that exploit the sequence- and structure-specific molecular mechanism of prion isoform interaction and/or conversion. Accordingly, the present invention provides methods for identifying compounds that bind to and inactivate PrP or otherwise behave as a prion antagonist. These compounds include "lead" peptide compounds and "derivative" compounds constructed so as to have the same or similar molecular structure or shape as the lead compounds, but that differ from the lead compounds either with respect to susceptibility to hydrolysis or proteolysis and/or with respect to other biological properties, such as increased affinity for PrP$^{Sc}$. The present invention also provides compositions comprising an effective amount of a prion antagonist, and more particularly a compound, that is useful for treating prion diseases.

Discovery of Peptides That Selectively Bind to PrP$^{Sc}$

The present invention provides methods for the identification of one or more peptides that binds to PrP$^{Sc}$ or a fragment. The invention provides for the rapid identification of peptides having the ability to interact with PrP$^{Sc}$. By screening individual peptides or other sources of peptides (e.g., peptide libraries) for binding to PrP$^{Sc}$, the invention allows for the identification of highly disparate protein sequences possessing equivalent functional activities, for example, the ability to identify peptides that bind PrP$^{Sc}$ using (1) peptides whose sequence or composition are not determined by the sequence or composition of PrP or (2) peptides whose sequence or composition are determined by the sequence or composition of PrP. The ability to identify and isolate peptides that bind to PrP$^{Sc}$ or a fragment thereof will prove invaluable in bringing new compounds into prion disease drug discovery programs.

PrP$^{Sc}$

PrP$^{Sc}$ is defined as a misfolded, prion disease-associated conformational isoform of the prion protein. Natural and experimental prion infections are recognized in (but not limited to) humans, sheep, goats, elk, deer, cattle, mice, and hamsters. The set of abnormal conformations (designated as, for example, PrP$^{Sc}$, PrP$^{BSE}$, PrP$^C$WD, PrP$^C$JD PrP$^{vCJD}$, depending upon the species of origin and prion strain; PrP$^{Sc}$ herein used generically) may possess partial protease resistance and high β sheet content. PrP$^{Sc}$ fragments are typically defined as portions of PrP$^{Sc}$ that are sufficiently large as to retain prion infectivity. The "protein only" theory of prion infectivity posits that molecules of PrP$^C$, a normal cell surface membrane protein, are converted to PrP$^{Sc}$ by a template-directed process catalyzed by the abnormal isoform.

Peptides

Peptides of the invention are, in general, molecules having an isoform-selective affinity for PrP$^{Sc}$ or a fragment thereof, with little or no binding to PrP$^C$. As described further below, the peptides of the invention are typically a fragment of PrP that preferably contains between 3 to 75 amino acid residues of PrP, or multimers thereof. Exemplary PrP amino acid sequences deposited at SwissProt include P04156 (human), P04925 (mouse), P97895 (golden hamster), P23907 (sheep), P52113 (goat), O02841 (white-tailed deer), P79142 (American elk), P10279 (bovine), Q01880 (bovine) and O18754 (cat). In other embodiments, the peptides of this invention include multimers of PrP sequences, composed of either sequences derived directly from reported PrP sequences, or containing amino acid substitutions homologous to the native sequence, as indicated by physicochemical similarity (e.g., Bacon and Anderson, J. Mol. Biol. 191: 153-61, 1986) or likelihood of substitution in evolution (e.g., Dayhoff et al., Atlas Protein Seq. Struc. 5: 345-352, 1978). These sequences include, but are not limited to, sequences containing PrP repeat motifs such as "YYX," "YYR," "YYQ," or "YYD." In particular embodiments, the peptides are in the form of MAPS, which are prepared according to standard methods (Tam, Proc Natl Acad Sci U.S.A. 85: 5409-13, 1988; Tam and Zevala, J. Immunol Methods 124: 53-61, 1989; Tam, J. Immunol Methods 196: 17-32, 1996), including 4-map and 8-map formats. One or more N-terminal cysteines for use as a coupling moiety may be added to the peptide sequence. Peptides can be produced not only by recombinant methods, but also by using chemical methods well known in the art. Solid phase peptide synthesis may be carried out in a batch-wise or continuous flow process which sequentially adds .alpha.-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-a-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. These processes are described, for example, in Merrifield, J. Am. Chem. Soc. 85:2149-2154, 1963; Atherton, Solid Phase Peptide Synthesis, IRL Press, Oxford (1989); and Erickson and Merrifield, In: The Proteins, (Neurath, H. and Hill, R. L., eds.) Academic Press, New York, vol. 2, pp. 255-527, 1976. Automated synthesis may also be carried out on machines such as the ABI 431A peptide synthesizer (ABI). A protein or portion thereof may be purified by preparative high performance liquid chromatography and its composition confirmed by amino acid analysis or by sequencing (Creighton, Proteins, Structures and Molecular Properties, W H Freeman, New York N.Y., 1984).

According to the methods of the invention, a peptide (which optionally is conjugated to a detectable label) or a plurality of peptides are contacted with PrP$^{Sc}$ to identify one or more peptides that selectively binds to PrP$^{Sc}$. If desired, random, combinatorial or conformationally-constrained peptide libraries can be used as a source of peptides, which can be screened to identify peptides that bind to, for example PrP$^{Sc}$. Many libraries are known in the art that can be used, e.g., chemically synthesized libraries or in vitro translation based libraries. Conformationally constrained libraries that can be used include but are not limited to those containing invariant cysteine residues which, in an oxidizing environment, cross-link by disulfide bonds to form cystines, modified peptides (e.g., incorporating fluorine, metals, isotopic labels, are phosphorylated, etc.), peptides containing one or more non-naturally occurring amino acids, non-peptide structures, and peptides containing a significant fraction of .gamma.-carboxyglutamic acid. Screening of peptide libraries or individual peptides for a peptide that selectively binds to PrP$^{Sc}$ or a fragment thereof, but not to PrP, is accomplished using any of a variety of commonly known methods.

The step of contacting PrP$^{Sc}$ or a fragment thereof with a peptide or with a plurality of polypeptides may be effected in a number of ways. For example, PrP$^{Sc}$ can be immobilized on a solid support and a solution of the plurality of polypeptides is contacted with the immobilized PrP$^{Sc}$. This procedure is similar to an affinity chromatographic process, with the affinity matrix being comprised of the immobilized PrP$^{Sc}$. The peptides having a selective affinity for PrP$^{Sc}$ are then purified by affinity selection. The nature of the solid support, process for attachment of PrP$^{Sc}$ to the solid support, solvent, and conditions of the affinity isolation or selection procedure are carried out according to conventional methods and are well known to those of ordinary skill in the art.

If the amino acid sequence is to be determined from the polypeptide itself, one may use microsequencing techniques. The sequencing technique may, if desired, include mass spectroscopy.

In certain situations, it may be desirable to wash away any unbound peptide from a mixture of the PrP$^{Sc}$ and the plurality of polypeptides prior to attempting to determine or to detect the presence of a selective affinity interaction (i.e., the presence of a recognition unit that remains bound after the washing step).

The degree of selective binding between PrP$^{Sc}$ (or a fragment thereof) and its interacting peptide may vary, generally falling in the range of about 1 nM to about 1 mM. In preferred embodiments of the present invention, the selective binding is on the order of about 10 nM to about 100 µM, more preferably on the order of about 100 nM to about 10 µM, and most preferably on the order of about 100 nM to about 1 µM. Binding is said to be selective when under similar experimental conditions a peptide exhibits higher affinity for PrP$^{Sc}$ than for PrP$^C$. The binding affinity may be quantitatively or qualitatively assessed by any method known in the art.

Screening for Interactions of PrP$^{Sc}$ With Peptides Whose Sequence or Composition are Not Determined By the Sequence or Composition of PrP The interaction of PrP$^{Sc}$ with a peptide may be due to physicochemical forces between the molecules unrelated to a specific sequence contained within PrP. Examples of such interactions include the following.

Hydrophobic Interactions

PrP$^{Sc}$ displays increased hydrophobicity in comparison to PrP$^C$, probably contributing to the poor solubility and increased aggregation tendency of the abnormal isoform. Moreover, increased molecular surface hydrophobicity is observed in recombinant PrP$^C$ induced by low pH and denaturants to develop increased beta sheet content reminiscent of PrP$^{Sc}$ (Swietnicki et al, J. Biol. Chem. 272:27517-27520, 1997). Hydrophobic moieties will bind to other hydrophobic moieties in aqueous environments, due to Van der Waals interactions induced by molecular proximity and an increase in entropy of water associated with the reduction of hydrophobic molecular surface (Lodish et al., eds., Molecular Cell Biology, Palgrave Publishers, 2000). Thus, peptides containing hydrophobic amino acids will bind selectively to PrP$^{Sc}$. Hydrophobic amino acids, graded from most to least hydrophobic (Kyte and Doolittle, J. Mol. Biol. 157:105-32, 1982), are phenylalanine, methionine, isoleucine, leucine, valine, cysteine; other hydrophobic amino acids (Engleman et al., Annu. Rev. Biophys. Biophys. Chem. 15:321-53, 1986) are tryptophan, alanine, threonine, glycine, and serine. It should be noted that excessive hydrophobicity of selected peptides may render them unusable in PrP$^{Sc}$-selective binding, for reasons of generalized protein adherence (including PrP$^C$) and neutralization of PrP$^{Sc}$ binding due to self-adherence prior to interaction with a sample. Thus, peptides containing amino acids of intermediate hydrophobicity may prove superior for this application, or hydrophobic amino acids interspersed with hydrophilic amino acids to enhance solubility in an aqueous sample.

Pi-Stacking Interactions

We have demonstrated that recombinant PrP subjected to denaturants and low pH displays more tyrosyl groups at the molecular surface than PrP$^C$, and that mono- and polyclonal antibodies directed against the PrP repeat motif tyrosine-tyrosine-arginine bind to PrP$^{Sc}$ but not PrP$^C$ from a number of species (see, for example, WO/0078344). PrP refolded in a disease-specific form is therefore believed to possess more solvent accessible tyrosine side chains than does PrP$^C$. Increased accessibility of surface tyrosyls can be exploited for isoform-specific affinity interactions by pi-stacking with aromatic amino acids contained in peptide reagents of this invention. Pi-stacking occurs through interaction of an electron-rich aromatic ring circumference with an electron poor aromatic ring center, which may be mediated by a displaced parallel interaction, or an edge-to-face or "T" interaction conformation (McGaughey et al, J. Biol. Chem. 273:15458-63, 1998). Aromatic residues classically thought to undergo pi stacking include tyrosine, tryptophan, and phenylalanine. Peptides containing aromatic amino acids will specifically interact with PrP$^{Sc}$ through pi-stacking with tyrosine or other aromatic residues exposed on the molecular surface of PrP$^{Sc}$.

Charge Interactions

PrP$^{Sc}$ displays more surface hydrophobicity than PrP$^C$, but charged or polar moieties can participate in specific interactions. Such charged and polar moieties potentially exposed to solvent on PrP$^{Sc}$ at physiological solutions and pH include glycans (particularly the negatively charged sialic acid residues terminating many glycan antennae; Endo et al., Biochemistry 28:8380-8, 1989) and charged amino acid side chains such as arginine, lysine, aspartate, and glutamate.

Beta Sheet Interactions

PrP$^{Sc}$ contains much more beta sheet conformation than does PrP$^C$. It is possible that peptides could adopt a beta strand conformation which would then be "incorporated" into the beta sheet-rich structure of PrP$^{Sc}$. Moreover, peptides constrained in a beta sheet conformation may constitute an affinity reagent selectively interacting with PrP$^{Sc}$. Parallel and antiparallel beta sheets are stabilized by hydrogen bonding between C=O groups on one strand and NH groups on an adjacent strand. Moreover, amino acids of beta strands in proteins often alternate between hydrophobic side chains buried in the protein interior, and hydrophilic side chains at the molecular surface. Sequence-constrained properties may therefore be mimicked by synthetic peptides or by structurally constrained peptides, which, in turn, may be exploited for specific affinity interactions with PrP$^{Sc}$. In this manner, the synthetic peptide may be regarded as an exogenous beta strand for domain swapping with the relevant endogenous PrP strand. 3D domain swapping has been recently recognized as a mechanism by which monomeric proteins may form multimeric assemblies (reviewed in Bennett et al, Protein Science, 4: 2455-2468, 1995).

Screening for Interactions of PrP$^{Sc}$ With Peptides Whose Sequence or Composition are Determined By the Sequence or Composition of PrP In another series of examples, the interaction of PrP$^{Sc}$ with a peptide may be due to physicochemical forces resulting from prion protein interaction with itself, dependent upon a specific sequence contained within PrP. It is possible that such self-self interactions drive the PrP$^C$ to PrP$^{Sc}$ conversion central to the propagation of prion infectivity.

In one example of the invention, peptides are constructed to mimic a domain of PrP that is involved in the molecular process of recognition and recruitment of PrP$^C$ by PrP$^{Sc}$. These interactions can utilize a number of intermolecular forces, such as ionic interactions, hydrogen bonding, hydrophobic interactions, and pi-stacking of aromatic residues. The invention particularly relates to diagnostic aids that contain a PrP motif, either as a peptide with a single motif, or tandem repeats of the motif. One such motif repeated three times in the PrP sequence comprises two sequential tyrosines in association with a C-terminal arginine at two sites (YYR), and a C-terminal glutamine or aspartate at the third site (YYQ/D). YYX motif sequences are conserved across a number of species including, but not limited to, bovine, man, sheep, mouse, and hamster. Poly- and monoclonal antibodies directed against YYR have been shown to immunoprecipitate PrP$^{Sc}$ specifically, establishing that motif side chains become differentially solvent accessible in the conformational conversion of the prion protein. See, for example, WO/0078344. The specific interaction of solvent exposed YYR motifs in PrP with a synthetic polyamino acid chain can therefore be exploited for selective recognition of PrP$^{Sc}$ in a biological sample.

In another aspect, the invention relates to short synthetic prion peptides (e.g., three to ten amino acids or four to twelve amino acids, inclusive) including amino acid side chains which are differentially exposed to solvent in PrP$^{Sc}$ but not PrP$^C$. Critical amino acid residues participating in this interaction can be identified and a specific artificial sequence (peptide) can be constructed to selectively bind PrP$^{Sc}$ and not PrP$^C$. Examples of motifs participating in the conversion of PrP$^C$ to PrP$^{Sc}$ (and thus potentially differentially solvent accessible in PrP$^{Sc}$) are to be found in the medical and biological literature (see, for example, Horiuchi et al., J. Biol. Chem. 276:15489-97, 2001).

Notably, amino acids from several groups often possess the potential to interact with proteins by several intermolecular forces. For example, tryptophan may interact by means of hydrophobic and pi-stacking interactions, and tyrosine may interact by aromatic pi-stacking and hydrogen bonding involving its hydroxyl group. Thus, another example of the invention is interaction with PrP$^{Sc}$ via a peptide modeled on the prion protein sequence, but with evolutionarily conserved amino acid substitutions.

To demonstrate the interaction of a PrP peptide with PrP$^{Sc}$, fifty μg of normal (N) or scrapie (Sc) hamster brain lysate was incubated with 100 μl of 17D10 antibody-coated tosyl-activated magnetic beads (17D10; FIG. 1, lanes 2 and 3), 100 μl of YYRRYYRYY (SEQ ID NO:2) peptide-coupled sulfolink resin (10-mer; FIG. 1, lanes 4 and 5), or 100 μl of a FIP control peptide-coupled sulfolink resin (control; FIG. 1, lanes 6 and 7) in binding buffer (PBS, 3% Igepal CA630 and 3% TWEEN®) for 2.5 hours at room temperature. The beads (or resin) were then washed with wash buffer (PBS, 2% Igepal CA630 and 2% TWEEN®) three times, and resuspended in gel loading buffer. The samples were run on 16% Tris Glycine gels, and blots developed with monoclonal 6H4 and goat anti-mouse IgG-HRP conjugate. With this repeat motif derived from the prion protein amino acid sequence, precipitation of the prion protein, PrP$^{Sc}$ derived from scrapie infected brain, is observed, but not the normal isoform, PrP$^C$ derived from normal brain (FIG. 1). The FIP control peptide precipitated neither isoform.

Figure 2:
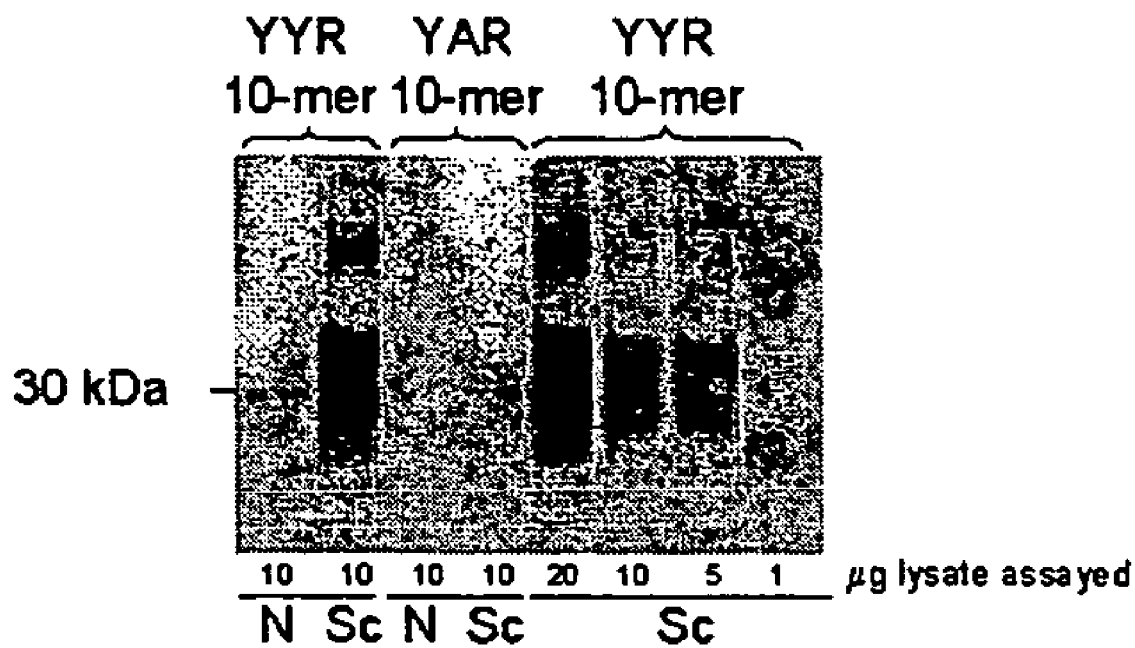
FIG. 2 shows that the YYRRYYRYY (SEQ ID NO:2) peptide captures PrP$^{Sc}$ in bovine brain lysates.

In addition, the interaction of the YYRRYYRYY (SEQ ID NO:2) peptide with bovine PrP$^{Sc}$ was examined (FIG. 2). Varying concentrations of BSE-positive (Sc) or negative (N) bovine brain lysate were incubated with 100 μl of tosyl-activated magnetic beads coated with cys-YYRRYYRYY (SEQ ID NO:2) ("YYR" 10-mer) or cys-YARRAYRAY ("YAR"; SEQ ID NO: 5; 10-mer) in IP binding buffer for 2.5 hours at room temperature. The beads were then washed with IP wash buffer three times, and resuspended in gel loading buffer. The samples were run on 4-12% NuPage MES gels, and blots developed with monoclonal 6H4 and goat anti-mouse IgG-HRP conjugate. The lane assignments are as follows: Lane 1, YYR 10-mer and 10 μg normal lysate; lane 2, YYR 10-mer and 10 μg BSE lysate; lane 3, YAR 10-mer and 10 μg normal lysate; lane 4, YAR 10-mer and 10 μg BSE lysate; lane 5, YYR 10-mer and 20 μg BSE lysate; lane 6, YYR 10-mer and 10 μg BSE lysate; lane 7, YYR 10-mer and 5 μg BSE lysate; lane 6, YYR 10-mer and 1 μg BSE lysate. These data indicate that the YYR-related affinity precipitation of PrP$^{Sc}$ is not species-restricted. It should be noted that although the YAR 10-mer coupled to tosyl beads failed to capture PrP$^{Sc}$ from BSE positive samples, biotinylated versions of this peptide coupled to strepavidin coated magnetic beads do function as effective capture reagents.

Figure 3:
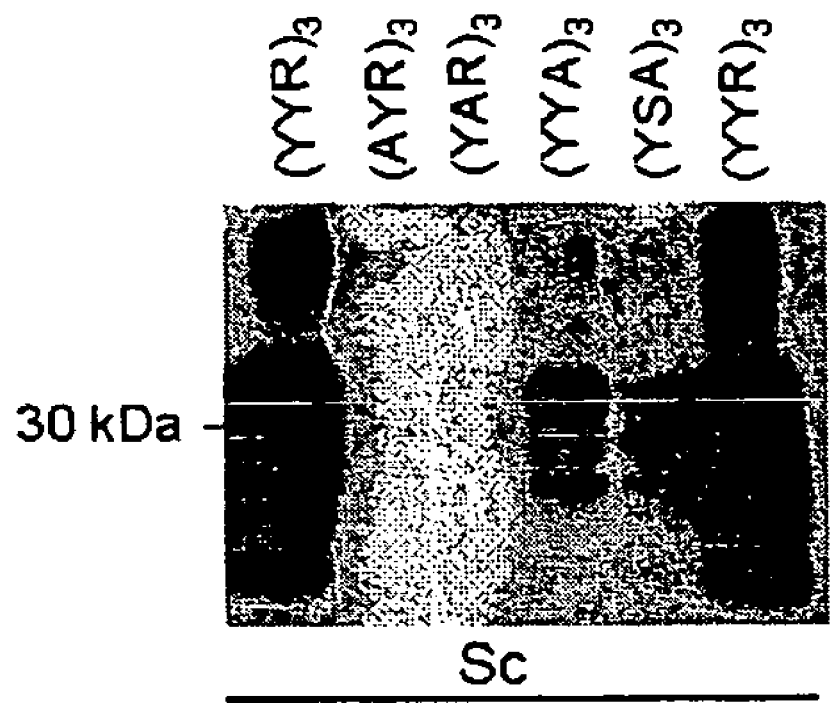
FIG. 3 shows that peptides related to the YYRRYYRYY (SEQ ID NO:2) peptide capture PrP$^{Sc}$ in mouse brain lysates.

To determine whether peptides related to the YYRRYYRYY (SEQ ID NO:2) (10-mer) peptide facilitate the capture of PrP$^{Sc}$, fifty μg of scrapie (Sc) mouse brain lysate was incubated with 100 μl of tosyl-activated magnetic beads coated with cys-YYRRYYRYY ("(YYR)$_3$; (SEQ ID NO:2) FIG. 3, lanes 1 and 6), cys-AYRRYARYA ("(AYR)$_3$"; SEQ ID NO: 6; FIG. 3, lane 2), cys-YARRAYRAY ("(YAR)$_3$"; (SEQ ID NO:5) FIG. 3, lane 3), cys-YYMYYAYY ("(YYA)$_3$; (SEQ ID NO:3) FIG. 3, lane 4), or cys-YSAASYASY ("(YSA)$_3$"; (SEQ ID NO:4) FIG. 3, lane 5) in IP binding buffer for 2.5 hours at room temperature. The beads were then washed with IP wash buffer three times, and resuspended in gel loading buffer. The samples were run on 16% Tris-glycine gels, and blots developed with monoclonal 6H4 and goat anti-mouse IgG-HRP conjugate. As shown in FIG. 3, precipitation of PrP$^{Sc}$ was observed with the YYR repeat sequence, and with YYA and YSA substitutions, but not with YAR or AYR repeats. These data suggest a critical role for tyrosine pairs, and/or a hydroxyl moiety of one tyrosine, in the affinity precipitation using peptides coupled to tosyl-activated beads. Biotinylated versions of the (YAR)$_3$ peptide, however, are effective capture reagents when coupled to streptavidin magnetic beads. Other peptide sequences that have been evaluated and shown to selectively bind PrP$^{Sc}$ in this format include, YARYARYAR, YRAARYRAY, bovine PrP (158-183) and bovine PrP (130-147). Peptides negative for PrP$^{Sc}$ selective capture include NHSTHNTGH (SEQ ID NO: 7), DRYYWY-FDV (SEQ ID NO: 8) and DEAYYKGWFAY (SEQ ID NO: 9).

Figure 4:
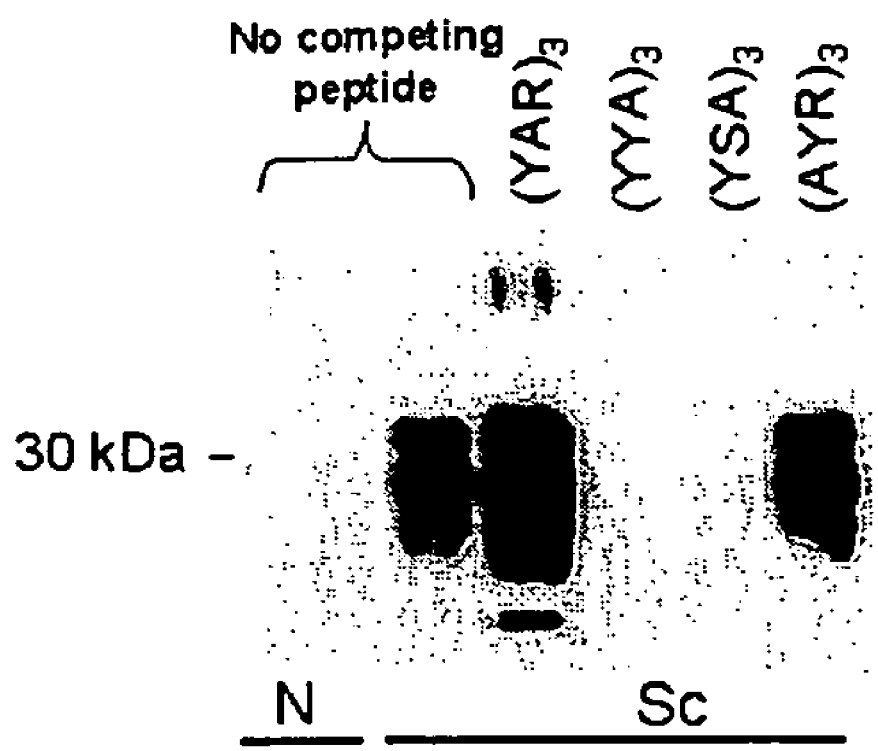
FIG. 4 shows that that the YYAAYYAYY (SEQ ID NO: 3) and YSAASYASY (SEQ ID NO: 4) peptides compete with YYRRYYRYY (SEQ ID NO:2)-linked beads for capture of mouse PrP$^{Sc}$.

The specificity of the peptide: PrP$^{Sc}$ was also studied in the following competition experiments. To demonstrate that the YYMYYAYY (SEQ ID NO:3) and YSAASYASY (SEQ ID NO:4) peptides compete with YYRRYYRYY (SEQ ID NO:2) beads for the capture of mouse PrP$^{Sc}$, 100 μl of tosyl-activated magnetic beads coated with cys-YYRRYYRYY (SEQ ID NO:2) were incubated over night at 4° C. with 500 μg/ml free peptide in IP binding buffer. Fifty μg of normal (N) or scrapie (Sc) mouse brain lysate was added to each sample, and the beads were then incubated for 2.5 hours at room temperature. The samples were then washed with IP wash three times, and resuspended in gel loading buffer. The samples were run on 16% Tris Glycine gels, and blots developed with monoclonal 6H4 and goat anti-mouse IgG-HRP conjugate. The data are shown in FIG. 4: lane 1, normal mouse lysate and no competing peptide; lane 2, Scrapie lysate and no competing peptide; lane 3, scrapie lysate and cys-YARRAYRAY (SEQ ID NO: 5) ("(YAR)$_3$"); lane 4, scrapie lysate and cys-YYAAYYAYY (SEQ ID NO: 3) ("(YYA)$_3$"); lane 5, scrapie lysate and cys-YSAASYASY (SEQ ID NO: 4) ("(YSA)$_3$"); lane 6, Scrapie lysate and cys-AYRRYARYA (SEQ ID NO: 6) ("(AYR)$_3$"). These data show that free YYMYYAYY (SEQ ID NO: 3) and YSAASYASY (SEQ ID NO: 4) compete with tosyl-activated YYRRYYRYY (SEQ ID NO: 2) beads for capture of PrP$^{Sc}$. Surprisingly, free YARRAYRAY (SEQ ID NO: 5) peptide failed to compete for binding even though biotinylated forms of the peptide are effective ligands for PrP$^{Sc}$. In any case, these data extend those exemplified in FIG. 2 in implicating paired tyrosines, particularly the hydroxyl moiety of the internal tyrosine, in the specific affinity interaction of YYR-related peptides with PrP$^{Sc}$.

Use

The peptides described herein may be used, for example, for the following diagnostic, therapeutic, vaccination, and decontamination purposes, as well as for screening for novel compounds that can be utilized to diagnose or combat prion diseases or decontaminate prion samples.

Diagnostics

The peptides disclosed herein find diagnostic use generally in the detection or monitoring of prion diseases. For example, the YYRRYYRYY (SEQ ID NO: 2) peptide may be used to monitor the presence or absence of PrP$^{Sc}$ in a biological sample (e.g., a tissue biopsy, a cell, or fluid) using standard and/or amplified detection assays. Such assays and methods may involve direct detection of PrP$^{Sc}$, and are particularly suited for screening large amounts of samples for the presence of PrP$^{Sc}$. For example, any of the peptides described herein may be detectably-labeled to measure peptide: PrP complex formation. If desired, because of the specificity of the peptides described herein for capturing PrP$^{Sc}$, pretreatment of a test sample with protease prior to analysis is optional. Any appropriate label which may be directly or indirectly visualized may be utilized in these detection assays including, without limitation, any epitope tag, radioactive, fluorescent, chromogenic (e.g., alkaline phosphatase or horseradish peroxidase), or chemiluminescent label, or a hapten (for example, digoxigenin or biotin) which may be visualized using a labeled, hapten-specific antibody or other binding partner (e.g., avidin). For example, using the peptides described herein, PrP$^{Sc}$ may be readily detected at the cell surface (e.g., a leukocyte) using standard flow cytometry methods such as those described herein. Samples found to contain increased levels of labeled complex compared to appropriate control samples are taken as indicating the presence of PrP$^{Sc}$, and are thus indicative of a prion-related disease.

In addition, novel compounds useful for diagnosing prion disease may be identified using the peptides of the invention. For example, combinatorial chemical libraries or small molecule libraries are screened to identify compounds having the ability to inhibit the binding interaction of one or more of the peptides described herein according to standard methods.

Such libraries may be derived from natural products, synthetic (or semi-synthetic) extracts, or chemical libraries according to methods known in the art. Those skilled in the field of drug discovery and development will understand that the precise source of compounds is not critical to the screening procedure(s) of the invention. Examples of natural compound sources include, but are not limited to, plant, fungal, prokaryotic, or animal sources, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds, i.e. aptamers. Synthetic compound libraries may be obtained commercially or may be produced according to methods known in the art. Furthermore, if desired, any library or compound is readily modified using standard chemical, physical, or biochemical methods.

Compounds that inhibit binding of a peptide at lowest concentration are referred to as "high affinity competitors" and are useful in the diagnostic methods of the invention. Such high affinity competitors that mimic the activity of the peptide are subsequently tested for efficient recognition and binding of PrP$^{Sc}$. Once identified, high affinity competitors may be coupled to solid substrates (for example, ELISA wells or beads) for use in the capture phase of virtually any diagnostic test for prion infection or, alternatively, in blocking format assays.

Vaccines

Peptides of the invention and mixtures and combinations thereof are also useful as active components of vaccines capable of inducing a prophylactic or therapeutic immune response against prion diseases in a host susceptible to and/or harboring infection. Routes of administration, antigen doses, number and frequency of injections will vary from species to species and may parallel those currently being used in the clinic and/or experimentally to provide immunity or therapy against other infectious diseases or cancer. For example, the vaccines are pharmaceutically acceptable compositions containing the peptide of this invention, its analogues or mixtures or combinations thereof, in an amount effective in the mammal, including a human, treated with that composition to raise immunity sufficient to protect the treated mammal from prion infection for a period of time. It is also possible that PrP$^{Sc}$-specific immunity prompted by immunization with peptides that include YYX amino acid residues (or YYR, YYD, or YYQ amino acid residues) or related compounds are useful to favor the degradation of PrP$^{Sc}$ or alleviate manifestations of the disease without affecting the expression or function of PrP$^C$ in the brain and other tissues, resulting in improvement of clinical status in clinically symptomatic humans with prion disease.

Different types of vaccines can be developed according to standard procedures known in the art. For example, a vaccine may be peptide-based, nucleic acid-based, bacterial- or viral-based vaccines. More specifically, with regard to peptide vaccines, peptides corresponding to the PrP$^{Sc}$-specific epitope or a functional derivatives thereof can be utilized as a prophylactic or therapeutic vaccine in a number of ways, including: 1) as monomers or multimers of the same sequence, 2) combined contiguously or non-contiguously with additional sequences that may facilitate aggregation, promote presentation or processing of the epitope (e.g., class I/II targeting sequences) and/or additional antibody, T helper or CTL epitopes to increase the immunogenicity of the PrP$^{Sc}$-specific epitope as a means to enhance efficacy of the vaccine, 3) chemically modified or conjugated to agents that would increase the immunogenicity or delivery of the vaccine (e.g., fatty acid or acyl chains, KLH, tetanus toxoid, or cholera toxin), 4) any combination of the above, 5) the above in combination with adjuvants, including but not limited to aluminum salts, saponins or triterpenes, MPL, and cholera toxin, and/or delivery vehicles, including but not limited to liposomes, VPLs or virus-like particles, microemulsions, attenuated or killed bacterial and viral vectors, and degradable microspheres, 6) administered by any route or as a means to load cells with antigen ex-vivo.

Examples of uses of nucleic-acid based vaccines as a prophylactic or a therapeutic include: 1) any nucleic acid encoding the expression (transcription and/or translation) of the PrP$^{Sc}$-specific epitope, 2) additional nucleic acid sequences that facilitate processing and presentation, aggregation, secretion, targeting (to a particular cell type) of the PrP$^{Sc}$-specific epitope, either translational fusions or independent transcriptional units, 3) additional nucleic acid sequences that function as adjuvants/immunomodulators, either translational fusions or independent transcriptional units, 4) additional antibody, T helper or CTL epitopes that increase the immunogenicity of the PrP$^{Sc}$-specific epitope or efficacy of the vaccine, either translational fusions or independent, 5) any combination of the above, 6) the above administered in saline ('naked' DNA) or in combination with an adjuvant(s), (e.g. aluminum salts, QS-21, MPL), immunomodulatory agent(s) (e.g. rIL-2, rGM-CSF, rIL-12), and/or nucleic acid delivery agents (e.g. polymer-, lipid-, peptide-based, degradable particles, microemulsions, VPLs, attenuated bacterial or viral vectors) using any route or ex vivo loading.

Attenuated or killed bacterial or viral vectors can be used to deliver either the antigen or DNA/RNA that codes for the expression of the antigen. These can also be used as a means to load cells with antigen ex vivo.

Vaccines are prepared according to standard methods known in the art, and will be readily applicable to any new or improved method for vaccine production.

Decontamination

PrP$^{Sc}$ can be adsorbed from biological fluids and tissues to neutralize prion infectivity prior to human use or as a prion disease prophylactic in animal feed using the peptides disclosed herein.

In still another aspect, the invention features methods for decontaminating PrP$^{Sc}$ from a biological sample. In a preferred embodiment, the method involves the steps of: (a) treating the biological sample with the peptide (or a fragment or analog thereof), the treatment permitting PrP$^{Sc}$ complex formation with the peptide; and (b) recovering the PrP complex from the biological sample. Such a decontamination procedure may also involve the use of perfusing a biological sample with peptide (or a fragment or analog thereof) coupled to biotin, hapten or epitope tag, such as FLAG or Myc, for the removal via streptavidin, or antibody affinity column chromatography or direct inactivation of PrP$^{Sc}$ by binding.

Accordingly, the methods and compositions described herein are useful for the decontamination of biological samples that are known or suspected of being contaminated with a prion, e.g. intended for transplantation. In particular, biological samples may be incubated with a peptide of the invention, and the complexes removed using standard methods. Alternatively, a peptide of the invention may be incubated with biological samples to complex with, and thereby inhibit the infectivity of prion.

Therapeutics

The invention further features a method of treating or preventing a prion disease in an animal (for example, a human, a bovine, sheep, pig, goat, dog, or cat). In one preferred embodiment, the method involves administering to the animal a therapeutically effective amount of PrP peptide identified according to the methods disclosed herein that blocks the conversion of PrP$^C$ to PrP$^{Sc}$, inhibits PrP$^{Sc}$: PrP aggregate formation, or blocks the recruitment of PrP$^C$ to PrP$^{Sc}$. In another aspect, the invention features a pharmaceutical preparation for the therapy and prevention of prion diseases comprising a PrP peptide of the invention or structurally related compounds, for example, compounds which exploit the PrP$^{Sc}$-specific exposure of peptides including amino acid residues YYX (or YYR, YYD, or YYQ amino acid residues) can be rationally designed or obtained from combinatorial libraries which mimic the interaction of a YYX containing peptide with anti-YYX peptides. These compounds are useful in prion diagnostics or as therapies for prion diseases. If desired, the peptides of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid. In addition, any of the peptides of the invention may be administered to a mammal, particularly a human, in one of the traditional modes (e.g., orally, parenterally, transdermally, or transmucosally), in a sustained release formulation using a biodegradable biocompatible polymer, or by using micelles, gels, and liposomes.

Moreover, small molecules derived from the structure of the YYR epitope(s), including but not limited to tyrosine side-chain derivatives, may block the conversion reaction. Finally, direct chemical modification of critical residues, such as enzymatic lysis of tyrosine rings, or covalent derivatization of tyrosine rings with bulky substitutions, may also disrupt the PrP$^C$ to PrP$^{Sc}$ conversion reaction.

For example, such compounds may be identified using the antibodies of the invention. Accordingly, combinatorial libraries or small molecule libraries or both (infra) are screened to identify compounds having the ability to inhibit the binding interaction of one or more of the peptides described herein according to standard methods. Compounds that inhibit binding of such molecules are useful in the therapeutic methods of the invention. Once identified, such compounds are tested for their ability to combat prion diseases in any appropriate model system.

Evaluation of whether a test antagonist (e.g., a peptide described herein) confers protection against the development of a prion disease in vivo generally involves using an animal known to develop such a disease (e.g., Chandler, Lancet 6:1378-1379, 1961; Eklund et al., J. Infectious Disease 117: 15-22, 1967; Field, Brit. J. Exp. Path. 8:129-239, 1969). An appropriate animal (for example, a mouse or hamster) is treated with the test compound according to standard methods, and a reduced incidence or delayed onset or progression of a prion-related illness, compared to untreated control animals, is detected as an indication of protection. The test compound may be administered to an animal which has previously been injected with a prion agent or, alternatively, the test compound may be tested for its ability to neutralize a prion agent by pre-incubating the prion and the compound and injecting the prion/compound mixture into the test animal. A molecule (e.g., an antagonist as described above) that is used to treat or prevent a prion disease is referred to as an "anti-prion therapeutic."

An anti-prion therapeutic according to the invention may be administered with a pharmaceutically-acceptable diluent, carrier, or excipient, in unit dosage form. For example, conventional pharmaceutical practice may be employed to provide suitable formulations or compositions to administer such anti-prion therapeutics to animals suffering from or presymptomatic for a prion disease, or at risk for developing a prion disease. Any appropriate route of administration can be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration.

Methods well known in the art for making formulations are found in, for example, "Remington's Pharmaceutical Sciences." Formulations for parenteral administration can, for example, contain excipients, sterile water, or saline, polyalkylene glycols such as polyethylene glycol, oils of vegetable origin, or hydrogenated napthalenes. Biocompatible, biodegradable lactide polymer, lactide/glycolide, or polyoxyethylene-polyoxypropylene copolymers can be used to control the release of the compounds. Other potentially useful parenteral delivery systems for anti-prion therapeutic compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate and deoxycholate, or can be oily solutions for administration in the form of nasal drops, or as a gel.

The methods of the present invention may be used to reduce or prevent the disorders described herein in any animal, for example, humans, domestic pets, zoo animals (such as tigers, exotic ruminants, and nonhuman primates), or livestock. Where a non-human animal is treated, the anti-prion therapeutic employed is preferably specific for that species.

In related aspects, the invention features therapeutic and diagnostic compounds identified according to any of the aforementioned methods.

Various publications are cited herein, the disclosures of which are incorporated by reference in their entireties.

We claim:

1. A method for detecting a $PrP^{Sc}$ in a biological sample, said method comprising the steps of: (a) contacting said biological sample with a peptide consisting of up to 25 amino acids and comprising $YYX^1X^2YYX^3YY$ (SEQ ID NO:1), wherein $X^1$, $X^2$ and $X^3$ are all R (SEQ ID NO:2) or wherein $X^1$, $X^2$, and $X^3$ are all A (SEQ ID NO:3) under conditions that allow for complex formation between said peptide and a $PrP^{Sc}$ polypeptide or fragment thereof, and (b) detecting said complex as an indication that said $PrP^{Sc}$ is present in said biological sample.

2. The method of claim 1, wherein said peptide does not substantially bind $PrP^C$.

3. The method of claim 1, wherein said peptide consists of $YYX^1X^2YYX^3YY$ (SEQ ID NO:1).

4. The method of claim 1, wherein said biological sample comprises a tissue or cell, a tissue or cell extract, a bodily fluid, or a biopsy.

5. The method of claim 1, wherein said $PrP^{Sc}$ is from a human, a livestock species, or a pet species.

6. The method of claim 1, wherein said peptide is covalently coupled to a detectable-label.

7. The method of claim 1, wherein said peptide is covalently coupled to a solid support or carrier.

8. The method of claim 1, wherein said complex is detected using an ELISA, RIA, western blotting, immunoprecipitation, fluorescence polarization, or flow cytometry.

9. The method of claim 1, wherein said $PrP^{Sc}$ in said biological sample is amplified $PrP^{Sc}$.

10. A method for generally diagnosing a prion disease in a mammal, said method comprising the steps of: (a) contacting a biological sample of said mammal with a peptide consisting of $YYX^1X^2YYX^3YY$ (SEQ ID NO:1), wherein $X^1$, $X^2$ and $X^3$ are all R (SEQ ID NO:2) or wherein $X^1$, $X^2$, and $X^3$ are all A (SEQ ID NO:3) under conditions that allow for complex formation between said peptide and a $PrP^{Sc}$ polypeptide or fragment thereof; and (b) detecting said complex, which if present indicates a prion disease in said mammal.

11. The method of claim 10, wherein said peptide does not substantially bind $PrP^C$.

12. The method of claim 10, wherein said biological sample comprises a tissue or cell, a tissue or cell extract, a bodily fluid, or a biopsy.

13. The method of claim 10, wherein said $PrP^{Sc}$ is from a human, a livestock species, or a pet species.

14. The method of claim 10, wherein said peptide is covalently coupled to a detectable-agent.

15. The method of claim 10, wherein said peptide is covalently coupled to a solid substrate.

16. The method of claim 10, wherein said complex is detected using an ELISA, RIA, western blotting, immunoprecipitation, fluorescence polarization or flow cytometry.

* * * * *

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Xaa is any amino acid.
<220> FEATURE:
<221> NAME/KEY: MISC_FEATURE
<222> LOCATION: (7)..(7)
<223> OTHER INFORMATION: Xaa is any amino acid.

<400> SEQUENCE: 1

Tyr Tyr Xaa Xaa Tyr Tyr Xaa Tyr Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Tyr Tyr Arg Arg Tyr Tyr Arg Tyr Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3
```

```
Tyr Tyr Ala Ala Tyr Tyr Ala Tyr Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Tyr Ser Ala Ala Ser Tyr Ala Ser Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Tyr Ala Arg Arg Ala Tyr Arg Ala Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Ala Tyr Arg Arg Tyr Ala Arg Tyr Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Asn His Ser Thr His Asn Thr Gly His
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Asp Arg Tyr Tyr Trp Tyr Phe Asp Val
1               5

<210> SEQ ID NO 9
<211> LENGTH: 11
<212> TYPE: PRT
<213> ORGANISM: Artificial Sequence
<220> FEATURE:
```

-continued

```
<223> OTHER INFORMATION: Synthetic peptide

<400> SEQUENCE: 9

Asp Glu Ala Tyr Tyr Lys Gly Trp Phe Ala Tyr
1               5                   10
```